Figure 1:
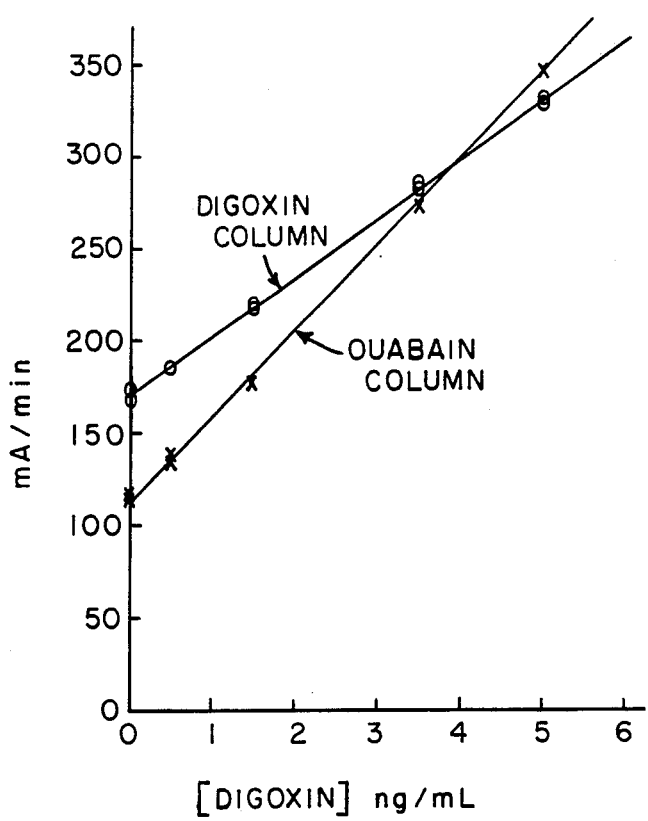

United States Patent [19]

Freytag et al.

[11] Patent Number: 4,551,426
[45] Date of Patent: Nov. 5, 1985

[54] HETEROGENEOUS IMMUNOASSAY FOR DIGOXIN USING OUABAIN AS A SEPARATION MEANS

[75] Inventors: William J. Freytag, Wilmington, Del.; Shung-Ho Chang, Encinitas, Calif.

[73] Assignee: E. I. Du Pont de Nemours and Company, Wilmington, Del.

[21] Appl. No.: 571,966

[22] Filed: Jan. 18, 1984

Related U.S. Application Data

[63] Continuation-in-part of Ser. No. 538,772, Oct. 3, 1983, abandoned.

[51] Int. Cl.[4] .................... G01N 33/54; G01N 33/56
[52] U.S. Cl. ......................................... 435/7; 435/14; 435/810; 436/512; 436/536; 436/541; 436/542; 436/804; 436/808; 436/815; 436/823
[58] Field of Search ............................ 435/7, 14, 810; 436/512, 536, 541, 542, 804, 808, 815, 823

[56] References Cited

U.S. PATENT DOCUMENTS

| | | | |
|---|---|---|---|
| 4,039,652 | 8/1977 | Adams | 436/541 X |
| 4,064,227 | 12/1977 | Brown | 436/541 X |
| 4,200,436 | 4/1980 | Mochida | 436/512 |
| 4,397,960 | 8/1983 | Moussebois | 436/512 |

OTHER PUBLICATIONS

"Methods in Enzymology", vol. 84, Immunochemical Techniques, Part D, J. J. Langone et al., eds., Chapt. 42 by V. P. Butler, Jr. et al., Immunoassay of Digoxin and Other Cardiac Glycosides, pp. 558-577, Academic Press, New York, 1982.

*Primary Examiner*—Sidney Marantz
*Attorney, Agent, or Firm*—George A. Frank; Gerald E. Deitch

[57] ABSTRACT

A heterogeneous immunoassay for digoxin. An excess of labeled anti-digoxin antibody is added to a test sample and the resulting reaction mixture is contacted with a solid phase having ouabain immobilized thereon. All the free, labeled antibody binds to the oubain. The eluted digoxin anti-digoxin antibody complex is measured for label activity. A competitive mode is also disclosed.

20 Claims, 1 Drawing Figure

1

HETEROGENEOUS IMMUNOASSAY FOR DIGOXIN USING OUABAIN AS A SEPARATION MEANS

RELATED APPLICATIONS

This application is a continuation-in-part of U.S. Ser. No. 538,772 filed Oct. 3, 1983, now abandoned.

TECHNICAL FIELD

This invention relates to an improved immunoassay for digoxin and, more specifically, to a noncompetitive heterogeneous immunoassay employing a labeled, monovalent or divalent anti-digoxin antibody as the indicator reagent and a column of immobilized ouabain as the means for effecting a separation.

BACKGROUND ART

A large and expanding market exists for clinical laboratory diagnostic tests capable of determining rapidly and accurately the concentration of digoxin present in biological fluids. Digoxin frequently is present at concentrations of nanomolar or less.

In recent years, a number of immunoassay techniques have been developed for the measurement of clinically important ligands. Typically, a competitive binding immunoassay consists of a conjugate of a labeling substance linked to a binding component which participates in a binding reaction to produce two species of the labeled conjugate, a bound species and a free species. The relative amounts of the labeled conjugate that result in the bound species and the free species are a function of the concentration of the ligand to be detected in the test sample.

Where the labeled conjugate in the bound species and that in the free species are essentially indistinguishable by the means used to measure the labeling substance, the bound species and the free species must be physically separated. This type of assay is referred to as heterogeneous.

The two most widely used heterogeneous immunoassays are the radioimmunoassay (RIA) and the enzyme linked immunosorbent assay (ELISA). In the RIA, a sample containing an unknown amount of antigen is mixed with a known amount of radiolabeled antigen and antibody. The system is allowed to react to near-equilibrium and then the antibody-bound antigen is separated from the unbound antigen. Since sample antigen competes with the labeled antigen for a limited number of antibody binding sites, the more the antigen in the sample, the less labeled antigen is in the bound fraction (or the more is in the unbound fraction). This process is generally time-consuming (1-3 hours) and labor intensive.

More recently, the RIA has been automated by immobilizing the antibody on a porous support. After the sample suspected of containing antigen is mixed with a known amount of labeled antigen, the sample is percolated through a column containing a limited number of immobilized antibody binding sites. Either the free or bound label can be quantified. Although rapid, this assay requires precise metering of antibody if it is to be reproducible.

RIA suffers from 2 major disadvantages: First, the labeling substance employed is a radioisotope which poses numerous problems associated with handling, storage, and disposal. Second, RIA is performed in a competitive mode (i.e., the analyte and the labeled analyte compete for a limited number of binding sites on the antibody), and therefore the antibody affinity constant limits the sensitivity of the assay, typically in the range of $10^{-8}M^1$ to $10^{-11}M^1$.

ELISA is similar in principle to RIA except that the labeling substance is an enzyme rather than a radioisotope. It will suffers from the limitation that sensitivity is a strict function of the antibody affinity constant.

Other labeling substances have been described in addition to isotopes and enzymes. These include fluorophores, coenzymes, bioluminescent materials, enzyme inhibitors, etc.

Various methods of effecting the separation step in heterogeneous immunoassays are known. These include filtration, centrifugation, chromatography, etc.

The use of an affinity column to effect the separation step has been described in French Patent Appl. No. 79 15992, published Jan. 9, 1981. It describes the use of a gel having coupled to it a ligand which has affinity for the labeling substance and which additionally has molecular sieving properties. The use of a gel having affinity for the ligand of interest rather than for the labeling substance and having molecular sieving properties is also disclosed. The assay described can be performed in a competitive or noncompetitive mode.

U.S. Pat. No. 4,298,687, issued Nov. 3, 1981 to Moes, discloses a heterogeneous immunoassay in which the substance to be determined is reacted with a labeled primary binding partner and the amount of unreacted binding partner is then determined by absorption on a solid phase endowed with specific binding properties for the primary binding partner. The primary binding partner is present in limited amount.

U.S. Pat. No. 3,654,090, issued Apr. 4, 1972, to Schuurs et al., describes a noncompetitive heterogeneous immunoassay for human chorionic gonadotropin (HCG) which uses an excess of enzyme-labeled divalent antibody and an immobilized HCG column to accomplish the separation step. This assay is limited in sensitivity by the fact that one cannot distinguish between an antibody with one molecule of HCG bound and an antibody with no HCG bound. Both species will be retained by the affinity column.

U.S. Pat. No. 4,134,792, issued Jan. 16, 1979 to Boguslaski et al., discloses a heterogeneous immunoassay in which the labeled specific binding partner for the ligand of interest is present in excess. The labeled specific binding partner is a divalent antibody and suffers from the same disadvantage cited above.

Girma et al., Brit. J. Haematol, volume 47, 269 (1981), describe a two-site immunoradiometric assay (IRMA) for coagulation factor VIII in which monovalent Fab fragments of antibodies are used. Their results indicate a tenfold higher sensitivity can be attained using monovalent rather than divalent antibodies.

U.S. Pat. No. 4,200,436, issued Apr. 29, 1980 to Mochida et al., discloses an immunoassay employing a labeled monovalent antibody in which immobilized antigen (the same antigen as that to be measured) is used to separate the bound and free fractions. Since it is primarily the bound fraction which is measured, this assay is usually performed in a competitive mode. Hence, sensitivity is limited by the affinity constant of the antibody when the assay is performed according to the preferred mode.

In some cases it is possible to substitute an analyte analogue for analyte in an immunoassay. In general, the performance is expected to be equivalent whether one uses analyte or analyte analogue. Unexpectedly, it has been found in the assay of this invention for digoxin that substitution of ouabain for digoxin as the immobilized antigen dramatically improves the sensitivity and precision of the assay. Although the exact mechanism responsible for this improvement is not known, it is believed to reside in the nature of the antigen-antibody interaction.

There is a need in the art for a heterogeneous immunoassay for digoxin, the sensitivity and precision of which are not limited by the affinity constant of the antibody.

DISCLOSURE OF INVENTION

The noncompetitive heterogeneous immunoassay of this invention is comprised of the following steps:

(a) forming a reaction mixture by contacting a molar excess of labeled, monovalent or divalent anti-digoxin antibody with a test sample suspected of containing digoxin, whereby a fraction of said antibody forms a complex with the digoxin and a fraction remains free;

(b) separating free antibody from the reaction mixture by contacting the reaction mixture with a solid phase comprising ouabain immobilized on a solid support, the oubain being present in an amount capable of binding all of the free antibody; and (c) measuring the amount of complex which elutes from the solid phase by measuring the label.

The amount of digoxin in the sample can then be determined by comparison with a standard curve.

In another aspect, the present invention is a competitive, heterogeneous immunoassay which is comprised of the following sequential steps:

(a) forming a reaction mixture by contacting a sample suspected of containing digoxin with a molar excess of ouabain immobilized on a solid phase;

(b) contacting the reaction mixture with a labeled, monovalent or divalent anti-digoxin antibody, said antibody being in molar excess over digoxin, but in molar deficiency relative to ouabain;

(c) allowing a reaction to take place whereby a fraction of the antibody forms a first complex with the digoxin and a second fraction forms a complex with the immobilized ouabain;

(d) separating the first fraction from the second fraction; and (e) determining the amount of label present in either the first or the second fraction.

DESCRIPTION OF THE INVENTION

In general, it is desirable to immunopurify the antibody prior to its use in an immunoassay. Again, the methods for isolation of IgG from animal serum, ascites fluid, or tissue culture medium and the methods for its immunopurification by affinity chromatography are known in the art. Briefly, an Ig fraction is prepared by ammonium sulfate precipitation. An IgG fraction is then prepared by ion exchange, gel filtration, or protein A chromatography. Affinity purification is effected by elution from an antigen column.

The antibody can be polyclonal or monoclonal. Monovalent antibodies are produced by methods known in the art. For example, Fab fragments are obtained by papain digestion of IgG; Fab' fragments are obtained by disulfide reduction of F(ab')$_2$ fragments obtained by pepsin digestion of IgG.

Any number of methods can be employed to couple the labeling substance to the antibody. The labeling substance can be enzyme, radioisotope, chromophore, fluorophore or any other substance which is capable of generating a detectable signal, either alone or in combination with other reagents. In general, one should couple at least one label to each antibody, preferably covalently, and in such a manner as to preserve the immunoreactivity of the antibody and the activity of the labeling substance. The free sulfhydryl groups present on Fab' fragments provide specific reactive groups for covalent attachment of the label. Heterobifunctional crosslinking reagents having maleimido- or thiopyridyl-groups are useful for this purpose. Generally, it is desirable that the final step in the synthesis of the labeled antibody be an immunopurification step to ensure retention of immunoreactivity.

Ouabain or a conjugate thereof can be immobilized on a suitable support by methods known in the art, e.g. Smith, T. W., Butler, V. P., Haber, E., Biochemistry, Volume 9, p. 331 (1970). In general, the support is chosen for its flow characteristics and can include, for example, beaded agarose, beaded dextran, polyacrylamide, or glass. The ouabain can be coupled covalently to the support, either directly or through a spacer arm which can be a protein, polyamino acid, or synthetic linker. Usually, the affinity column material is discarded after one use, but it is possible to recycle it if desired. It is generally undesirable for the support to possess molecular sieving properties since, should the labeled antibody become dissociated from sample analyte, molecular sieving will tend to reduce the likelihood of their finding each other again.

In the noncompetitive mode, the assay of this invention can be performed as follows: A known volume of patient sample, usually 5 $\mu$L to 500 $\mu$L of serum, containing an unknown amount of digoxin is mixed with a solution containing an amount of labeled, monovalent or divalent antibody known to be in excess over digoxin. Usually the labeled antibody will be present in approximately 10-100 molar excess over digoxin. Digoxin and antibody are preincubated for a specified length of time, usually at least 5 minutes and not more than 30 minutes, at a fixed temperature between 4° C. and 45° C., usually 37° C. A known volume (usually 5 $\mu$L to 500 $\mu$L) of this solution containing digoxin-bound antibody and unbound antibody is passed through a column, preferably of dimensions 2 mm × 10 mm, consisting of ouabain immobilized on a porous support. Sufficient ouabain-coupled support is used to bind all of the free labeled antibody. The column is eluted at a flow rate of 0.2-4.0 mL per minute with a suitable buffer, usually 1-5 mL total volume. The fraction which elutes from the column contains labeled antibody complexed with digoxin from patient serum. The activity of the label in this fraction is then measured. Alternatively, one can discard this fraction and elute the retained antibody from the column with a chaotropic agent or by extremes of pH. In the first instance, the amount of label is directly proportional to the concentration of digoxin in the sample. In the second, it is inversely proportional.

The assay of this invention can be performed manually or it can be adapted to a variety of automated or semi-automated instrumentation, such as the aca ® discrete clinical analyzer manufactured by E. I. du Pont de Nemours and Company, Inc., Wilmington, Dela. In this case, patient sample and excess labeled, monovalent or divalent antibody are preincubated outside the instrument. A known volume of this mixture is automatically injected into an analytical test pack (described in U.S. Pat. No. Re. 29,725 to Johnson et al., reissued Aug. 8, 1978, and incorporated herein by reference) in the filling station of the instrument, followed by a volume of buffer sufficient to bring the final in-pack volume to 5 mL. The sample mixture percolates through a column of ouabain immobilized on a porous support located in the pack header and is eluted directly into the pack. The eluted fraction contains labeled antibody complexed with analyte from patient serum. The pack is automatically processed at 37° C. with addition of reagents required for the signal generating reaction at either breaker/mixer I or breaker/mixer II and photometric readout of the signal.

The assay of this invention can also be performed in a competitive mode, by which is meant that the antibody is simultaneously, rather than sequentially, exposed to the sample digoxin and the ouabain.

In the competitive mode, the assay can be performed as follows: An aliquot of sample suspected of containing digoxin, generally 10 to 100 $\mu$L is added to a test tube containing a molar excess of ouabain immobilized on a solid phase (generally 100 to 1000 $\mu$L packed volume of an affinity column resin such as a cross-linked agarose or dextran). Then, a monovalent or divalent, labeled anti-digoxin antibody solution is added in an amount which is in molar excess over the highest value of digoxin expected in the sample, but in molar deficiency relative to the ouabain. The volume of antibody solution is generally 5 to 50 $\mu$L. The reaction mixture so formed is incubated at a temperature between 23° C. and 45° C., preferably 37° C. for 15 to 60 minutes, preferably 15 minutes with gentle agitation. Antibody-digoxin complex is then separated from antibody/immobilized-ouabain complex. If an affinity resin is used, centrifugation at 2000×g for about three minutes is preferred. The supernatant fluid is then aspirated. Either the amount of label adsorbed on the solid phase or the amount of label in the supernatant fluid can be measured to determine the amount of digoxin initially present in the text sample. If the label is an enzyme, the measurement can be carried out by reacting the enzyme with its substrate to produce a detectable product. Nonenzyme labels such as fluorophores, chromophores and radioisotopes can be measured by techniques well known in the art.

The advantages of using ouabain, rather than digoxin on the solid phase are illustrated by the following examples in which both digoxin (analyte) and ouabain (analyte analogue) columns were prepared under a variety of experimental conditions and their performance in an affinity column-mediated immunometric assay for digoxin were evaluated in terms of background, sensitivity, and precision. Although the optimal conditions for synthesis of each resin were different, the best ouabain resin consistently outperformed the best digoxin resin.

While only ouabain is specifically exemplified herein, contemplated equivalents are digitoxin, deslanoside, digoxigenin and strophanthin.

EXAMPLE 1

A. Synthesis of Monovalent Antibody-Enzyme Conjugate

Digoxin-specific antibodies were immunopurified directly from whole rabbit serum using a ouabain-HSA immunoadsorbent.

Ouabain was attached to an agarose matrix through a protein (HSA, human serum albumin) spacer arm. The first step involved the synthesis of a ouabain-albumin conjugate. Ouabain (0.56 mmols dissolved in 20 mL of water) was oxidized with sodium metaperiodate (1.02 mmols) for 1 hour at room temperature in the dark. Quantitative oxidation was verified by thin layer chromatography on silica gel G plates developed in ethylacetate:methanol:$H_2O$ (75:25:1). The excess periodate was removed by passing the aqueous mixture over a 3 mL column of DOWEX AG-1X8 ion exchange resin. Quantitative recovery of ouabain was verified by following radiolabeled (tritiated) ouabain. The solution of oxidized ouabain was buffered to pH 9.5 with the addition of 0.4 mL of 5% $Na_2CO_3$ and combined with 20 mL of HSA solution (28 mg/mL). After 45 minutes, the conjugate was reduced by the addition of 0.3 gm of sodium borohydride freshly dissolved in 20 mL of water. Three hours later, 8 mL of 1M formic acid was added to lower the pH to 6.5. After 1 hour at pH 6.5, the pH was raised to pH 7.5 with 1M $NH_4OH$. The entire reaction mixture was dialyzed exhaustively against distilled water, and then finally against 0.015M sodium phosphate buffer, pH 7.8, 0.15M NaCl. The conjugate was concentrated on an Amicon PM-30 membrane to 4.2 mg/mL. Protein concentration was determined by the method of Lowry, which is known in the art.

The ouabain-HSA conjugate was immobilized on Affi-Gel®10 (Bio-Rad Laboratories) using the procedure described in the Bio-Rad manual. 25 mL of Affi-Gel®10 was washed with 75 mL of ice-cold water. The gel was added to the dialyzed ouabain-HSA conjugate and allowed to mix on a rocker overnight at 4° C. The excess active ester groups were quenched by adding 0.1 mL of 1M ethanolamine, pH 8.0, for 1 hour at room temperature. Finally, the gel was washed extensively with distilled water, and then in turn: 500 mL of 0.5M NaCl; 400 mL 0.1M glycine, pH 2.5; 300 mL 2.5M $NH_4SCN$; 1000 mL phosphate buffered saline. The ouabain affinity resin was packed into a column (0.7×15 cm) to a bed volume of 6 mL and equilibrated with phosphate-buffered saline. Antiserum (10 mL of Cappel anti-digoxin serum at 4.5 mg/mL monospecific antibody) was applied at a flow rate of <1 mL per minute. The column was washed with phosphate-buffered saline until the absorbance at 280 nm reached baseline (<0.01). Antibody was then eluted from the column with 60 mL of 3M $NH_4SCN$ (pH 7.5) and immediately dialyzed against 4×2-L changes of phosphate-buffered saline at 4° C.

Twenty-seven mL of affinity-purified antidigoxin antibodies were concentrated to 2.7 mL on an Amicon stirred-cell apparatus (PM-30 membrane). The final protein concentration was 10 mg/mL. The sample was dialyzed against 1000 mL of 0.1M sodium acetate, pH 4.5, for 4 hours at 4° C. After dialysis, 20 $\mu$L of a 10 mg/mL solution of pepsin, dissolved in the same sodium acetate buffer, was added and the temperature raised to 37° C. for 20 hours. After this digestion period, the sample was clarified by a brief centrifugation and then chromatographed on a Sephadex G-150 column (1.5×90 cm) equilibrated in 0.015M sodium phosphate (pH 7.4), 0.15M NaCl (phosphate buffered saline). The column fractions containing the (Fab')$_2$-fragments, identified by gel electrophoresis, were pooled (19.2 mL) and then concentrated to 2.7 mL by pressure filtration (PM-30 Amicon membrane). After concentration, the (Fab')$_2$-fragments were reduced to their corresponding Fab'-fragments by adding 55 μL of a 1M dithiothreitol solution. The reduction was performed at 25° C. for 90 minutes followed by dialysis at 4° C. against 0.15M NaCl, 0.015M sodium phosphate, pH 5.6 (2×1000 ml).

The Fab' fragments so produced were then reacted with a 20-fold molar excess of m-maleimidobenzoic acid N-hydroxy succinimide ester (MBS). Eighty-five microliters of a 79 mM solution of MBS in tetrahydrofuran was added to the 2 mL solution of Fab' fragments and reacted for 1 hour at 25° C. under argon. The mixture was desalted on a Sephadex G-25 (cross-linked, beaded dextran having 5000 dalton exclusion limit) column (1.5 cm×40 cm) in phosphate buffered saline. The derivatized Fab' fragments, which eluted in the void volume, were pooled and combined with 2 mL of β-galactosidase at 12 mg/mL in phosphate buffered saline at 4° C. After 16 hours, this solution was concentrated to 2 mL on an Amicon PM-30 pressure filtration stirred-cell followed by column chromatography on Sepharose 4B-CL (cross-linked, macroporous agarose in bead form having 1–5×10$^6$ dalton exclusion limit in a 1.5 cm×90 cm column). The Fab'-β-galactosidase conjugate was eluted with the free β-galactosidase. The entire peak of enzyme activity was pooled and subsequently immunopurified on the ouabain affinity column. The procedure for immunopurification was as follows: Pooled column fractions from the Sepharose 4B-CL column were eluted through the ouabain affinity column (1.0 cm×7.0 cm), followed by 100 mL of phosphate buffered saline. The Fab'-β-galactosidase conjugate was then eluted with 50 mL of 23 mM ouabain in phosphate buffered saline. This eluate represented the final reagent and was dialyzed against 6×4 L of phosphate buffered saline at 4° C.

B. Synthesis of Ouabain and Digoxin Resins

Ouabain and digoxin were each coupled separately to Sephadex G-10 (beaded dextran available from Pharmacia Fine Chemicals) in various ratios via an organic spacer moiety, triethylenetetraamine (TETA).

Ouabain (20–325 mg) was dissolved in distilled water and oxidized for 2 hours at 25° C. by the addition of a fivefold molar excess of sodium metaperiodate. At the end of that time, the reaction was stopped by passing each solution over a 5 mL column of Dowex 1-X8 (a Cl$^-$ ion exchange resin) which removes the excess periodate. The eluates were collected and brought to a final concentration of 0.1M sodium phosphate, pH 7.0 by addition of a concentrated stock solution. TETA (50–125 mg) was added to each solution (see Table IA) and the pH of the final solution adjusted to pH 7.0. The solutions were incubated for 1 hour at 25° C., at the end of which time 30 mg of sodium cyanoborohydride was added. The resultant solutions were stirred at 25° C. for 48 hours.

The same procedure as outlined above for ouabain was followed for digoxin with the exception that digoxin was dissolved in 30% ethanol. Experimental details are given in Table IB.

Each of the conjugates (9 lots of ouabain-TETA and 9 lots of digoxin-TETA) was then coupled to Sephadex G-10 by the following procedure: 210 g of Sephadex G-10 was swollen in 1 L of distilled water. The resin was then washed 3 times with 1 L of water per wash. Finally, the resin was oxidized by suspension in 1 L of sodium metaperiodate (10 g/L). After 1 hour at 25° C., the resin was allowed to settle, the supernatant fluid was withdrawn, and the resin was washed on a sintered glass funnel with approximately 3 L of 0.25M sodium phosphate, pH 7.0. The resultant resin was divided into 25 mL portions and a portion mixed with each lot of conjugate synthesized above. After 1 hour of mixing, sodium cyanoborohydride (30 mg) was added to each portion of resin plus conjugate. The resultant suspensions were mixed at 25° C. for 64 hours at which time the resin was allowed to settle, the supernatant fluid was withdrawn, and the resins were washed (each portion separately) with 300 mL of water, 300 mL of 0.5M NaCl, and 500 mL of 0.15M sodium phosphate, pH 7.1. Each portion of resin was packed into aca ® discrete clinical analyzer analytical columns (0.5×8 cm, 1.8 mL per column). The columns in turn were placed in the headers of aca ® discrete clinical analyzer analytical test packs containing 7 mg of o-nitrophenyl-β-D-galactopyranoside (ONPG) in dimple 6.

C. Comparison of the Various Lots of Ouabain-TETA-Sephadex and Digoxin-TETA-Sephadex Each lot of resin synthesized in (B) above was evaluated on the aca ® discrete clinical analyzer according to the following protocol: Ten picomoles of β-galactosidase-labeled anti-digoxin Fab', synthesized in (A) above, was added to a 100 μL sample of pooled human serum containing either 0 or 5 ng/mL digoxin. After a 10 minute incubation at 25° C., the antibody-sample mixture was automatically injected into an aca ® discrete clinical analyzer analytical test pack described above and eluted through the column in the pack header. Sample was followed by 2 mL of 0.15M sodium phosphate, pH 7.8. The column flow rate was 34 μL/sec. The pack was then filled at needle position 2 (which bypasses the column) with an additional 2.9 mL of water. ONPG was released from breaker/mixer II approximately 3½ minutes later. Enzymatic activity was measured at 405 nm 29 and 46 sec after addition of substrate.

Table II compares the performance of all 18 lots of resin in terms of background (Table IIA) and sensitivity (Table IIB). Background was defined as the change in absorbance at 405 nm when the sample contained 0 ng/mL digoxin; under those conditions all of the labeled antibody should have remained bound to the column. Sensitivity was defined as the separation, i.e. change in absorbance at 405 nm, between 0 and 5 ng/mL digoxin.

While the backgrounds were generally lower when the column consisted of digoxin-TETA-Sephadex, the sensitivity was always better when the column consisted of ouabain-TETA-Sephadex. The best ouabain resin had a sensitivity of 0.158 absorbance units/min, while the best digoxin resin gave only 0.110 absorbance units/min. These resins, denoted by asterisks in Table IIB, were chosen for further study.

D. Precision

The resins denoted by asterisks in Table II, one consisting of ouabain-TETA-Sephadex and the other of digoxin-TETA-Sephadex, were further evaluated in terms of precision in an assay for digoxin. Packs were run exactly as described above using samples which contained 0, 1, or 3.4 ng/mL digoxin. At least 13 packs were run at each drug concentration and the mean (X), standard deviation (S.D.), and percent coefficient of variation (C.V.) determined. These are shown in Table III.

At 1 ng/mL digoxin, which is the medical decision level for this drug, precision of measurement was significantly improved for the ouabain column versus the digoxin column. Using a digoxin column, a person with a serum level of 1 ng/mL digoxin could easily be misidentified, leading to a possible overdose (or underdose) of the drug. Since digoxin is not effective at concentrations below 1 ng/mL and is toxic at concentrations much above that, the consequences of such an error in measurement could be severe. For this reason, use of a ouabain column in lieu of a digoxin column forms the basis of the present invention.

TABLE IA
Amounts of Ouabain and TETA Used in Resin Synthesis

| Lot No. | Ouabain (mg) | TETA (mg) |
|---|---|---|
| OU-A | 325 | 125 |
| OU-B | 195 | 75 |
| OU-C | 130 | 50 |
| OU-D | 125 | 125 |
| OU-E | 75 | 75 |
| OU-F | 50 | 50 |
| OU-G | 50 | 125 |
| OU-H | 30 | 75 |
| OU-I | 20 | 50 |

TABLE IB
Amounts of Digoxin and TETA Used in Resin Synthesis

| Lot No. | Digoxin (mg) | TETA (mg) |
|---|---|---|
| DG-A | 325 | 125 |
| DG-B | 195 | 75 |
| DG-C | 130 | 50 |
| DG-D | 125 | 125 |
| DG-E | 75 | 75 |
| DG-F | 50 | 50 |
| DG-G | 50 | 125 |
| DG-H | 30 | 75 |
| DG-I | 20 | 50 |

TABLE IIA
Comparison of Ouabain and Digoxin Resins: Background

| | Background (A/min) | |
|---|---|---|
| Lot No. | Ouabain (mg) | Digoxin |
| A | .234 | .042 |
| B | .254 | .108 |
| C | .261 | .318 |
| D | .111 | .044 |
| E | .121 | .206 |
| F | .124 | .311 |
| G | .164 | .137 |
| H | .166 | .224 |
| I | .159 | .268 |

TABLE IIB
Comparison of Ouabain and Digoxin Resins: Sensitivity

| | Sensitivity (A/min/5 ng/mL) | |
|---|---|---|
| Lot No. | Ouabain (mg) | Digoxin |
| A | .030 | .008 |
| B | .019 | — |
| C | .015 | .013 |
| D | .158* | .012 |
| E | .148 | .011 |
| F | .148 | .047 |
| G | .106 | .033 |
| H | .108 | .087 |
| I | .112 | .110* |

TABLE III
Comparison of Resins OU-D and DG-I: Precision

| | OU-D | DG-I |
|---|---|---|
| | 1 ng/mL Digoxin | |
| $\overline{X}$ (ng/mL) | 0.83 | 0.96 |
| S.D. (ng/mL) | 0.14 | 0.53 |
| % C.V. (ng/mL) | 17 | 55 |

TABLE III-continued
Comparison of Resins OU-D and DG-I: Precision

| | OU-D | DG-I |
|---|---|---|
| | 3.4 ng/mL Digoxin | |
| $\overline{X}$ (ng/mL) | 3.4 | 3.4 |
| S.D. (ng/mL) | 0.09 | 0.37 |
| % C.V. (ng/mL) | 2.5 | 11 |

EXAMPLE 2

A. Synthesis of Divalent (F(ab')$_2$) Antibody Enzyme Conjugate

One milliliter of affinity purified antidigoxin F(ab')$_2$-fragments [preparation described in Example 1] (2.85 mg/mL protein in 0.015M sodium phosphate, 0.15M NaCl, 1 mM EDTA, pH 7.0) was mixed at 23°–25° C. with 9.1 μL of a 60 mM solution of succinimidyl 4-(N-maleimido-methyl)cyclohexane-1-carboxylate (SMCC) dissolved in dimethylformamide. After 60 minutes the reaction was stopped by desalting the solution on a Sephadex G-25 column (1.5 cm × 30 cm) equilibrated in the same sodium phosphate-NaCl-EDTA solution. The protein which eluted in the void volume was collected and concentrated to 1 mL using an Amicon stirred-cell concentrator (PM-30 membrane). Twenty-four mg of β-galactosidase dissolved in 1 mL of 0.05M Tris•HCl, 0.15M NaCl, 1 mM MgCl$_2$, pH 7.5 was added to the F(ab')$_2$-SMCC adduct and allowed to react for 20 hours at 4° C. The reaction was quenched by the addition of 10 μL of a 0.1M solution of 2-mercaptoethanol for 1 hour at 4° C. The F(ab')$_2$-β-galactosidase conjugate was separated from the unreacted β-galactosidase by chromatography on a Sepharose 4B column (1.5 cm × 90 cm) equilibrated in 0.05M Tris•HCl, 0.15M NaCl, 1 mM MgCl$_2$, pH 7.5 at 4° C.

B. Synthesis of Ouabain and Digoxin Resins

Ouabain and digoxin were each coupled separately to Sephadex G-10 at optimized ratios via bovine serum albumin (BSA).

(1) Ouabain-BSA was prepared by dissolving 5 g of ouabain-octahydrate in 500 mL of hot distilled water (70° C.). After the solution was allowed to cool to 25° C., 7.3 g of sodium metaperiodate was added followed by continuous mixing for 2 hours at 25° C. in the dark. The oxidation was then stopped by passing the mixture through a 250 mL bed of Dowex (1-X8) anion exchange resin. The eluate was collected and combined with a solution of bovine serum albumin (10 gm/500 mL) dissolved in 1M sodium phosphate buffer, pH 7.0. After 1 hour at 25° C., 0.64 g of sodium cyanoborohydride was added with stirring and the mixture was allowed to incubate for 72 hours at 25° C. The uncoupled ouabain was removed from the mixture by dialyzing the ouabain-BSA conjugate solution against running distilled water for 24 hours and then against 20 volumes of 0.015M sodium phosphate buffer, pH 7.0 at 4° C. The final ionic strength of the conjugate solution was adjusted to 0.25M by adding 14.6 g of NaCl prior to coupling to the Sephadex resin.

(2) Coupling of Ouabain-BSA to Sephadex G-10

Sephadex G-10 (420 g) (Pharmacia Fine Chemicals) was allowed to swell in 2000 mL of distilled water for >1 hour. Resin fines were removed by decanting and resuspension with 3×2000 mL of water. The resin was then oxidized by resuspension in 1000 mL of water containing 20 g of dissolved sodium metaperiodate. After 10 minutes, the resin was washed with 5×2000 mL of water followed by 4000 mL of 0.25M sodium phosphate buffer, pH 7.0. The decanted resin was resuspended in 1000 mL of the ouabain-BSA solution (from above), allowed to mix for one hour at 25° C. and then mixed with 0.66 g of sodium cyanoborohydride. After 72 hours the resin was washed thoroughly with 4000 mL of 0.1% sodium dodecyl sulfate in water, 12 L of distilled water, and then 4000 mL of 0.15M sodium phosphate buffer, pH 7.1. The final resin was slurry packed into small columns (0.5 cm×7 cm) for use in automated analysis in the DuPont aca ® discrete clinical analyzer.

(3) Digoxin-BSA was prepared by dissolving 1.25 g of digoxin in 75 mL of ethanol and then combining this solution with 150 mL of water containing 1.83 g of sodium metaperiodate. After two hours at 25° C. with stirring, the oxidation was stopped by passing the mixture through a bed (100 mL) of Dowex (1-X8) anion exchange resin. The eluate was combined with a solution of bovine serum albumin (2.5 g) dissolved in 0.1M sodium phosphate, pH 8.5. Sodium cyanoborohydride (0.24 g) was then added and the mixture was mixed for 48 hours at 25° C. Free unconjugated digoxin was removed by dialysis against running distilled water for two days and then against 20 volumes of 0.015M sodium phosphate buffer, pH 7.0 at 4° C.

(4) Coupling of Digoxin-BSA to Sephadex G-10

Sephadex G-10 (50 g) was allowed to swell in 250 mL of distilled water for >1 hour. Resin fines were removed by decanting and resuspension. The resin was then oxidized by resuspension in 250 mL of water containing 5 g of dissolved sodium metaperiodate. After 10 minutes, the resin was washed with 5×250 mL of water followed by 1000 mL of 0.1M sodium phosphate buffer, pH 8.5. The decanted resin (~125 mL settled bed volume) was slurried in 125 mL of 0.1M sodium phosphate buffer, pH 8.5 containing 125 mg of sodium cyanoborohydride. After 24 hours of constant mixing the resin was washed with 3×500 mL of water, 500 mL of 0.15M sodium phosphate, pH 7.8, and then resuspended in 125 mL of 0.15M sodium phosphate, pH 8.5 at 4° C. Acetic anhydride (1.25 mL) was added to the slurry and allowed to react for 30 minutes at 4° C. with mixing. The resin was washed thoroughly with 1 L of 0.5M NaCl, 4 L of distilled water, and 2 L of 0.15M sodium phosphate, pH 7.1. The final resin was slurry packed into small columns (0.5 cm×8 cm) designed for placement into the headers of aca ® discrete clinical analyzer test packs.

C. Comparison of the Digoxin-BSA-Sephadex and Ouabain-BSA-Sephadex Resins Using a Divalent Antibody Enzyme Conjugate.

Both resin lots were compared under identical conditions. F(ab')$_2$-$\beta$-galactosidase, synthesized in (A) above, (2.6 picomoles in 200 $\mu$L of buffer) was added to 200 $\mu$L of normal human serum calibrators containing various amounts of digoxin (0, 0.5, 1.5, 3.5, and 5.0 ng/mL). After a 10 minute incubation period at 25° C., the entire antibody-sample mixture was automatically injected into an aca ® discrete clinical analyzer test pack and eluted through the column in the pack header. Sample was followed by 2 mL of 0.15M sodium phosphate, pH 7.8. The column flow rate was 34 $\mu$L/sec. The pack was then filled at needle position 2 (which bypasses the column) with an additional 2.6 mL of water. ONPG was released from breaker/mixer II approximately 3.5 minutes later. Enzymatic activity was measured at 405 nm 29 and 46 sec after addition of substrate.

FIG. 1 and Table IV compares the performance of the two optimized digoxin-BSA-Sephadex and ouabain-BSA-Sephadex resins in terms of background and slope sensitivity (FIG. 1) and precision (Table IV).

While both resin lots allowed linear dose responses with the F(ab')$_2$-$\beta$-galactosidase conjugate, the ouabain-resin exhibited both a lower background (32% lower) and a greater slope sensitivity (47% greater). Both a lower background and a higher slope sensitivity are preferred for better assay performance and accuracy. In addition, the assay precision was markedly better for the ouabain resin than for the digoxin resin (Table IV). Individual pack assays were run exactly as described above at two digoxin levels, 0.5 ng/mL and 1.5 ng/mL. At least 12 packs were run at each drug concentration and the mean (X), standard deviation (S.D.) and the percent coefficient of variation (C.V.) was determined.

TABLE IV

COMPARISON OF OUABAIN AND DIGOXIN RESINS FOR PRECISION

| | Ouabain Column | Digoxin Column |
|---|---|---|
| 0.5 ng/mL Digoxin | | |
| X (ng/mL) | 0.47 | 0.43 |
| S.D. (ng/mL) | 0.04 | 0.07 |
| % C.V. (ng/mL) | 8.1 | 14.2 |
| 1.5 ng/mL Digoxin | | |
| X (ng/mL) | 1.52 | 1.54 |
| S.D. (ng/mL) | 0.05 | 0.20 |
| % C.V. (ng/mL) | 3.0 | 13.1 |

We claim:

1. A noncompetitive immunoassay for the measurement of digoxin in a test sample, said assay comprising the steps of:
   (a) forming a reaction mixture by contacting a molar excess of labeled monovalent or divalent antidigoxin antibody with the test sample, whereby a fraction of said antibody forms a complex with the digoxin and a fraction remains free; and
   (b) contacting the reaction mixture with a solid phase having ouabain immobilized thereon, the ouabain being present in an amount capable of binding all of the free antibody, whereby the free antibody is bound to the solid phase; and
   (c) measuring the amount of complex which elutes from the solid phase by measuring the activity of the label.

2. The immunoassay of claim 1 wherein the label is an enzyme, radioisotope, chromophore or fluorophore.

3. The immunoassay of claim 1 wherein the monovalent antibody is an Fab fragment or Fab' fragment.

4. The immunoassay of claim 1 wherein the divalent antibody is an F(ab')$_2$ fragment.

5. The immunoassay of claim 1 wherein the solid phase is beaded agarose, beaded dextran, polyacrylamide or glass.

6. The immunoassay of claim 5 wherein the solid phase is packed in a column.

7. The immunoassay of claim 1 wherein the solid phase is beaded dextran, the monovalent antibody is an Fab' fragment and the label is $\beta$-galactosidase.

8. The immunoassay of claim 1 wherein the solid phase is beaded dextran, the divalent antibody is an F(ab')$_2$ fragment and the label is $\beta$-galactosidase.

9. The immunoassay of claim 7 wherein the measurement step (c) is performed by contacting the eluted $\beta$-galactosidase labeled, Fab' anti-digoxin antibody/- digoxin complex with o-nitrophenyl-β-D-galactopyranoside.

10. The immunoassay of claim 8 wherein the measurement step (c) is performed by contacting the eluted β-galactosidase labeled, F(ab')$_2$ anti-digoxin antibody/digoxin complex with o-nitrophenyl-β-D-galactopyranoside.

11. A competitive immunoassay for the measurement of digoxin in a test sample, said assay comprising the sequential steps of:
   (a) forming a reaction mixture by contacting a sample suspected of containing digoxin with a molar excess of ouabain immobilized on a solid phase;
   (b) contacting the reaction mixture with a labeled, monovalent or divalent anti-digoxin antibody, said antibody being in immunochemical excess over digoxin, but in immunochemical deficiency relative to ouabain;
   (c) allowing a reaction to take place whereby a fraction of the antibody forms a first complex with the digoxin and a second fraction forms a complex with the immobilized ouabain;
   (d) separating the first fraction from the second fraction; and
   (e) measuring the amount of label present in either the first or the second fraction.

12. The immunoassay of claim 11 wherein the label is an enzyme, radioisotope, chromophore or fluorophore.

13. The immunoassay of claim 11 wherein the monovalent antibody is an Fab fragment or Fab' fragment.

14. The immunoassay of claim 11 wherein the divalent antibody is an F(ab')$_2$ fragment.

15. The immunoassay of claim 11 wherein the solid phase is beaded agarose, beaded dextran, polyacrylamide or glass.

16. The immunoassay of claim 11 wherein the solid phase is beaded dextran, the monovalent antibody is an Fab' fragment and the label is β-galactosidase.

17. The immunoassay of claim 11 wherein the solid phase is beaded dextran, the monovalent antibody is an F(ab')$_2$ fragment and the label is β-galactosidase.

18. The immunoassay of claim 16 wherein the measurement step (e) is performed by contacting the fraction to be measured with o-nitrophenyl-β-D-galactopyranoside.

19. The immunoassay of claim 17 wherein the measurement step (e) is performed by contacting the fraction to be measured with o-nitrophenyl-β-D-galactopyranoside.

20. A test kit for measuring the amount of digoxin in a liquid sample, comprising:
   (a) a labeled anti-digoxin antibody; and
   (b) a solid phase having ouabain bound thereto; and
   (c) directions for the use of said kit.

* * * * *